United States Patent
Kubota

(10) Patent No.: US 10,048,410 B2
(45) Date of Patent: *Aug. 14, 2018

(54) LIGHT-SHIELDING FILM FOR OPTICAL ELEMENT AND OPTICAL ELEMENT HAVING LIGHT-SHIELDING FILM

(71) Applicant: CANON KABUSHIKI KAISHA, Tokyo (JP)

(72) Inventor: Reiko Kubota, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 204 days.

This patent is subject to a terminal disclaimer.

(21) Appl. No.: 14/597,070

(22) Filed: Jan. 14, 2015

(65) Prior Publication Data
US 2015/0125689 A1    May 7, 2015
US 2016/0363701 A9    Dec. 15, 2016

Related U.S. Application Data

(63) Continuation of application No. 13/026,001, filed on Feb. 11, 2011, now Pat. No. 8,958,155.

(30) Foreign Application Priority Data

Feb. 12, 2010 (JP) ................................. 2010-029514
Jan. 7, 2011 (JP) ................................. 2011-002163

(51) Int. Cl.
| | | |
|---|---|---|
| G02B 5/00 | (2006.01) | |
| C04B 14/30 | (2006.01) | |
| G02B 5/04 | (2006.01) | |
| C09D 7/40 | (2018.01) | |
| C09D 7/61 | (2018.01) | |
| C09D 163/00 | (2006.01) | |
| C09D 7/41 | (2018.01) | |

(Continued)

(52) U.S. Cl.
CPC ............ *G02B 5/003* (2013.01); *C04B 14/022* (2013.01); *C04B 14/305* (2013.01); *C04B 14/306* (2013.01); *C04B 14/325* (2013.01); *C09D 7/41* (2018.01); *C09D 7/61* (2018.01); *C09D 7/66* (2018.01); *C09D 7/67* (2018.01); *C09D 7/69* (2018.01); *C09D 163/00* (2013.01); *G01N 21/39* (2013.01); *G02B 1/10* (2013.01); *G02B 5/04* (2013.01); *Y10T 428/25* (2015.01); *Y10T 428/256* (2015.01); *Y10T 428/265* (2015.01)

(58) Field of Classification Search
None
See application file for complete search history.

(56) References Cited

U.S. PATENT DOCUMENTS

| | | | | |
|---|---|---|---|---|
| 5,714,286 A | * | 2/1998 | Uchikawa | G02F 1/133512 430/20 |
| 2009/0246650 A1 | * | 10/2009 | Fujimori | G03F 7/0007 430/7 |
| 2009/0280416 A1 | * | 11/2009 | Einaga | G03F 7/0007 430/7 |

OTHER PUBLICATIONS

Machine translation of JP2003-161804. Retrieved Aug. 22, 2013.*
Wypych, G. "Handbook of Fillers". ChemTec Publishing, (2000); pp. 15-177.*

* cited by examiner

*Primary Examiner* — Prashant J Khatri
(74) *Attorney, Agent, or Firm* — Canon U.S.A. Inc., IP Division

(57) ABSTRACT

A light-shielding film for optical element includes at least a resin and a colorant. The light-shielding film for optical element has an average extinction coefficient of 0.03 or more and 0.15 or less as an average of extinction coefficients of the whole light-shielding film for light having wavelengths ranging from 400 to 700 nm.

9 Claims, 3 Drawing Sheets

(51) Int. Cl.
*C04B 14/32* (2006.01)
*C04B 14/02* (2006.01)
*G02B 1/10* (2015.01)
*G01N 21/39* (2006.01)

LIGHT-SHIELDING FILM FOR OPTICAL ELEMENT AND OPTICAL ELEMENT HAVING LIGHT-SHIELDING FILM

CROSS REFERENCE TO RELATED APPLICATIONS

This application is a Continuation of U.S. patent application Ser. No. 13/026,001 filed Feb. 11, 2011, which claims priority to Japanese Patent Application No. 2011-002163 filed Jan. 7, 2011 and Japanese Patent Application No. 2010-029514 filed Feb. 12, 2010, all of which are hereby incorporated by reference herein in their entireties.

BACKGROUND OF THE INVENTION

Field of the Invention

The present invention relates to a light-shielding film for optical element that is applied to an optical apparatus, such as a camera, binoculars, a microscope, or a semiconductor exposure apparatus, and relates to an optical element.

Description of the Related Art

A light-shielding film for optical element is a coating film formed on a surface of, for example, glass or plastic. The optical element may be a lens, a prism, or another optical glass element, but, in this specification, the light-shielding film will be described using a lens as an example.

As shown in FIG. 1, the light-shielding film 1 for optical element is formed on an appropriate outer portion of a lens 2 serving as the optical element. Some of incident light, such as incident light 3, passes through the lens 2 as transmitted light 4. On the other hand, oblique incident light, such as incident light 5, strikes the light-shielding film 1. If the light-shielding film 1 is not provided, the light that struck the outer portion of the lens 2 is inner-surface-reflected and exits to the outside of the lens 2 as image-unrelated inner-surface-reflected light 6, which causes flare, ghost, etc. to deteriorate the image quality. Occurrence of the inner-surface-reflected light 6 due to the oblique incident light 5 can be reduced by providing the light-shielding film 1, which can prevent flare and ghost to inhibit disadvantageous effects on an image.

FIG. 2 is a schematic view illustrating how inner-surface-reflected light travels. As shown in FIG. 2, incident light 3 travels in the lens 2 and becomes first reflected light 8 at the interface 21 with the light-shielding film 1. The transmitted light 9 traveled in the light-shielding film 1 becomes second reflected light 10 at the interface 22 between the light-shielding film 1 and air. Therefore, in the inner-surface reflection, the first reflection light 8 and the second reflection light 10 are involved.

Recently, along with a reduction in lens size and an improvement in performance, the designed clearance between a lens and a lens barrel has been reduced. Accordingly, if a light-shielding film for optical element has a thickness that is equivalent to those of existing films, since the clearance is small, the lens may not be incorporated into a lens barrel. Therefore, in order to set a lens provided with a light-shielding film into a narrow clearance, the light-shielding film for optical element needs to be reduced in the thickness. In addition, a thinner light-shielding film can decrease the stress, resulting in a reduction in deformation of the lens.

Japanese Patent Publication No. 47-32419 describes an example of the light-shielding film that absorbs light with coal tar, carbon black, and dye while improving the refractive index with the coal tar. Japanese Patent Laid-Open No. 2007-183444 describes an example of the light-shielding film that absorbs light with coal tar and dye while improving the refractive index with the coal tar. Japanese Patent Laid-Open No. 07-82510 describes in this coating film, the content of the inorganic black particle is 10 to 60 parts by weight, because a content not larger than 10 parts by weight cannot sufficiently increase the refractive index of the light-shielding film, resulting in a large difference between the refractive indices of the light-shielding film and an optical element not to inhibit inner-surface reflection.

In order to inhibit the above-described inner-surface reflection, it is necessary to decrease the first reflected light 8 and the second reflected light 10. In order to decrease the reflection at the first interface, it is effective to decrease the difference between the refractive indices of the light-shielding film 1 and the lens 2. That is, it is necessary that the light-shielding film for optical element have a refractive index near that of the lens. In order to decrease the reflection at the second interface, it is necessary to make the light-shielding film 1 sufficiently black for absorbing the transmitted light 9 that transmitted to the light-shielding film 1. That is, the light-shielding film 1 needs to have a degree of blackness that can sufficiently absorb the transmitted light entered inside the light-shielding film.

However, an increase in absorption by increasing the degree of blackness of the light-shielding film 1 causes a problem in that the first reflected light 8 increases. The absorption of the light-shielding film 1 can be also increased by increasing the thickness of the light-shielding film 1, but an increase in the thickness inhibits the above-described reduction in lens size and improvement in performance. The light-shielding film for optical element described in Japanese Patent Publication No. 47-32419 contains 15 wt % or more and 36 wt % or less of carbon black and 15 wt % or more and 36 wt % or less of a dye, which sufficiently increases the refractive index and reduces the difference between the refractive indices of the light-shielding film and the lens. However, since the absorption of the light-shielding film is high, the reflection at the interface between the lens and the light-shielding film cannot be sufficiently inhibited.

In the light-shielding film for optical element described in Japanese Patent Laid-Open No. 2007-183444, the refractive index is increased by coal tar to reduce the difference between the refractive indices of the light-shielding film and the lens. In addition, the absorption is small due to the low concentration of the dye, which can reduce the reflection at the interface between the lens and the light-shielding film. However, since the absorption is small, in order to inhibit the reflection at the interface between the light-shielding film and air, the thickness of the film must be increased.

In the light-shielding film for optical element described in Japanese Patent Laid-Open No. 07-82510, the inorganic black particle content is controlled in the range of 10 to 60 parts by weight in order to sufficiently increase the refractive index of the light-shielding film. This light-shielding film can have a high refractive index, but the degree of absorption of the light-shielding film is low. Therefore, the first reflected light 8, which is light reflected at the interface between the light-shielding film and air, cannot be sufficiently inhibited.

SUMMARY OF THE INVENTION

The present invention provides a light-shielding film for optical element, having a small thickness and being low in inner-surface reflection, and also provides an optical element having the light-shielding film, being low in inner-surface reflection.

The light-shielding film for optical element of the present invention contains at least a resin and a colorant and has an average extinction coefficient of 0.03 or more and 0.15 or less as an average of extinction coefficients of the whole light-shielding film for light having wavelengths ranging from 400 to 700 nm (when the light-shielding film is composed of two or more layers, an average extinction coefficient of the light-shielding film as a whole).

Further features of the present invention will become apparent from the following description of exemplary embodiments with reference to the attached drawings.

DESCRIPTION OF THE EMBODIMENTS

Preferred embodiments of the present invention will be described below.

First, a constitution of a light-shielding film for optical element according to the present invention will be described. Then, a constitution of materials of the light-shielding film showing satisfactory inhibition of inner-surface reflection, even if it is reduced in thickness, will be described.

Constitution of Light-Shielding Film for Optical Element

The light-shielding film for optical element according to the present invention contains at least a resin and a colorant and has an average extinction coefficient of 0.03 or more and 0.15 or less as an average of extinction coefficients of the whole light-shielding film for light having wavelengths ranging from 400 to 700 nm.

Figure 1:
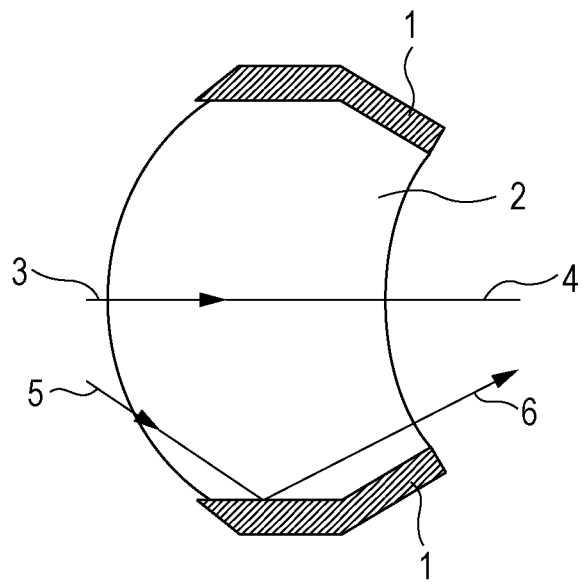
FIG. 1 is a cross-sectional view illustrating a light-shielding film for optical element formed on a lens.
Figure 2:
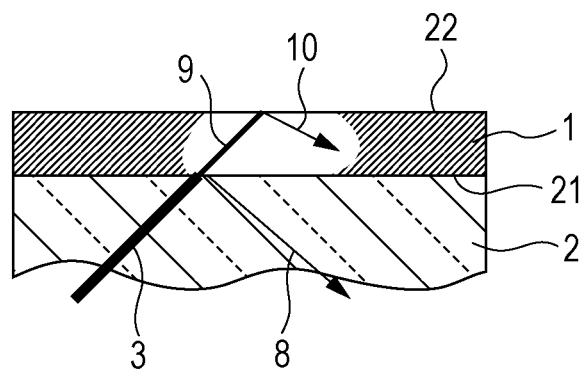
FIG. 2 is a schematic view illustrating how inner-surface-reflected light travels in a light-shielding film.

The principle of the inner-surface reflection will be described in more detail with reference to FIG. 2. As described above, the inner-surface reflection mainly occurs at two interfaces 21 and 22. That is, the incident light 3 travels in the lens 2 and becomes first reflected light 8 at the interface 21 between the lens 2 and the light-shielding film 1. The transmitted light 9 traveled in the light-shielding film 1 becomes second reflected light 10 at the interface 22 between the light-shielding film 1 and air.

The first reflected light 8 can be reduced by decreasing the difference between the refractive indices of the light-shielding film 1 and the lens 2. The reason for that inner-surface reflection is reduced by decreasing the difference between the refractive indices is, as shown in Equation (1) below, the reflectance R of the interface between the light-shielding film 1 and the lens 2 is determined by the difference between the refractive index $n_0$ of the lens 2 and the refractive index $n_1$ of the light-shielding film 1, and the smaller the difference is, the smaller the reflectance R is. Furthermore, since the light-shielding film 1 is black and absorbs light, it is necessary to determine the reflectance with considering the absorbance. When the absorbance of the light-shielding film is brought into consideration, the reflectance R is represented by an equation considering the extinction coefficient (attenuation coefficient) k as shown by Equation (1).

In this specification, the extinction coefficient k is a factor defining a quantity of light absorbed by a material.

$$R = \frac{|N_1 - N_0|^2}{|N_1 + N_0|^2}$$

$$= \frac{(n_1 - n_0)^2 + k^2}{(n_1 + n_0)^2 + k^2}$$

Equation (1)

In the equation, N represents the complex refractive index of a refractive index n. The refractive index n of a light-shielding film is represented by the complex refractive index N shown by Equation (2) obtained by adding the extinction coefficient k representing the absorption factor to the imaginary part i.

$$N = n - ik$$

Equation (2)

n represents the refractive index, and i represents the imaginary part.

The reflectance R is increased with the extinction coefficient k, when the extinction coefficient k representing the absorption factor k is considered.

That is, in order to reduce the inner-surface reflection at the interface between the lens and the light-shielding film having a light-absorbing property, it is necessary to reduce the difference between refractive indices of the light-shielding film and the lens and to reduce the value of extinction coefficient k. Since the bleeding range of light is about one fourth of the wavelength, the complex refractive index N can be increased by reducing the extinction coefficient in the area approximately 0.1 to 0.175 μm from the lens interface as low as possible.

The second reflected light 10 can be reduced by absorbing the transmitted light 9 traveling in the light-shielding film.

In the light-shielding film of the present invention, the extinction coefficient of the whole light-shielding film (when the light-shielding film is composed of two or more layers, the extinction coefficient represents the average of the extinction coefficients of the layers) is 0.03 or more and 0.15 or less, preferably 0.03 or more and 0.1 or less. When the extinction coefficient is smaller than 0.03, the quantity of reflected light at the interface between the light-shielding film and air is large, resulting in a deterioration in antireflection function. When the extinction coefficient is larger than 0.15, reflection at the interface between the lens and the light-shielding film is large. As long as the light-shielding film has an extinction coefficient of 0.03 or more and 0.15 or less, the light-shielding film may contain dye alone or may contain a small amount of pigment having a high extinction coefficient in addition to dye. Furthermore, the light-shielding film may contain inorganic black particles having a d-line refractive index of 2.2 or more and 3.5 or less alone as long as the extinction coefficient of the light-shielding film is 0.03 or more and 0.15 or less.

The light-shielding film is used in contact with an optical element. The extinction coefficient of the light-shielding film on the side that is in contact with the optical element can be smaller than the average extinction coefficient of the whole light-shielding film. Specifically, the extinction coefficient of the light-shielding film 1 can be lower on the side where the light-shielding film 1 and the lens 2 are in contact than the average extinction coefficient of the whole light-shielding film.

The extinction coefficient of the light-shielding film on the side being in contact with the lens can be specifically decreased, for example, by forming the light-shielding film with two or more layers containing different concentrations of dye or by adding both dye and pigment to the light-shielding film, but the method is not limited thereto.

Figure 3:
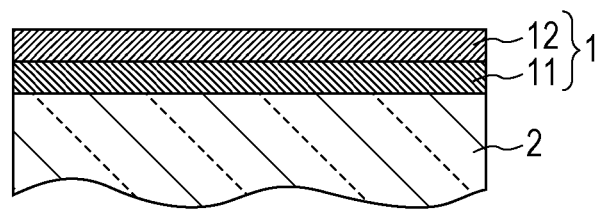
FIG. 3 is a schematic view illustrating a light-shielding film in which the dye concentration on the side adhering to a lens is lower than that as a whole.

For example, the light-shielding film 1 composed of two or more light-shielding layers containing different concentrations of dye can be obtained, as shown in FIG. 3, by forming a light-shielding layer 11 containing dye in a lower concentration and, after hardening of the layer, forming a light-shielding layer 12 containing dye in a higher concentration. Here, the thickness of the light-shielding layer 11 containing a lower concentration of the dye can be larger than one fourth of the wavelength of light (100 nm or more, when the wavelength is 400 nm) considering the bleeding distance of light, that is, the thickness can be about 0.1 µm or more considering the wavelength range of visible light. The method of forming a difference in concentration of dye is not limited to the above.

In the light-shielding film for optical element of the present invention, the ratio of a minimum transmittance to a maximum transmittance, (minimum transmittance)/(maximum transmittance), for light with wavelengths ranging from 400 to 700 nm can be 0.7 or more. If the ratio is smaller than 0.7, which causes occurrence of unevenness of inner-surface reflection depending on light wavelength and also causes a deterioration in color tone to degrade the appearance of the light-shielding film.

The average thickness of the light-shielding film for optical element of the present invention can be 2 µm or more and 30 µm or less, preferably 2 µm or more and 10 µm or less. When the thickness is 10 µm or less, the effect of preventing inner-surface reflection can be higher than that of a known coating film containing a small amount of dye, and even when the thickness is 2 µm, the effect of preventing inner-surface reflection can be maintained. However, when the thickness of the light-shielding film is smaller than 2 µm, as described above with reference to FIG. 2, since light reflection 10 occurs at the interface between the light-shielding film and air, the inner-surface reflection becomes large. If the thickness of the light-shielding film is larger than 10 µm, since light is sufficiently absorbed, the inner-surface reflection is low. Therefore, the thickness may be 30 µm or more as long as it does not cause a problem from the standpoint of lens design. However, a thickness of 30 µm or more may cause a problem in optical design, such that the lens cannot be incorporated into a lens barrel.

Material Constitution

Materials constituting the light-shielding film of the present invention will now be described.

The light-shielding film of the present invention contains at least a resin, a colorant, and non-black particles. The colorant is dye, a mixture of dye and pigment, or inorganic black particles having a d-line refractive index of 2.2 or more and 3.5 or less and giving an extinction coefficient of 0.03 or more and 0.15 or less when they are contained in a light-shielding film. The inorganic black particles have high light resistance compared with dye and are therefore suitable for application that requires high light resistance. Note that the term "degree of blackness" in the present invention is a ratio of a minimum transmittance to a maximum transmittance, (minimum transmittance)/(maximum transmittance), for light having wavelengths ranging from 400 to 700 nm.

The black pigment and the inorganic black particles in the present invention each have a degree of blackness of 0.7 or more.

The pigment used in the present invention is particles insoluble to solvents and is a black material that absorbs visible light having wavelengths ranging from 400 to 700 nm. The pigment can have a high average extinction coefficient. Examples of the material that is insoluble to solvents and is black and has a high extinction coefficient include, but not limited to, black pigments composed of at least one selected from the group consisting of carbon black, copper-manganese complex oxide, titanium black, and copper oxide.

The average particle diameter of the pigment can be 0.1 µm or more and 10 µm or less. Here, the average particle diameter of the pigment is that of actual sizes of particles present in a film, that is, when the pigment particles are aggregated, the size is that of the aggregate. Therefore, the primary particle diameter of the pigment may be smaller that 0.1 µm, as long as the average particle diameter after aggregation is 0.1 µm or more. The pigment is usually contained in a film in an aggregated form. Accordingly, the average particle diameter may be smaller than 0.1 µm as long as the average particle diameter after aggregation is 0.1 µm or more. The pigment is usually contained in a film in an aggregated form, but if the average particle diameter after aggregation is smaller than 0.1 µm, the compatibility of the pigment with a resin is increased, which allows the particles to easily reach the side being in contact with the lens. If the pigment reaches the interface with the lens, since the extinction coefficient of the pigment is high, the extinction coefficient of the interface is increased, resulting in an increase in inner-surface reflection. On the other hand, when the average particle size after aggregation is larger than 10 µm, the thickness of the light-shielding film is increased. This may cause a problem that the lens cannot be incorporated into a lens barrel.

The dye is a material that absorbs visible light having wavelengths ranging from 400 to 700 nm and is soluble to an appropriate solvent. Organic materials that are not classified as dye are also included as long as they satisfy the requirements. In order to regulate the ratio of a minimum transmittance to a maximum transmittance, (minimum transmittance)/(maximum transmittance), of the light-shielding film for light having wavelengths ranging from 400 to 700 nm to 0.7 or more, one kind of dye may be used, or two or more kinds of dye, such as black, red, yellow, or blue dye, may be mixed to control absorption wavelength. The dye can be azo dye, which is abundant in colors, but may be anthraquinone dye, phthalocyanine dye, stilbenze dye, pyrazolone dye, thiazole dye, carbonium dye, or azine dye. Furthermore, dye containing a metal, such as chromium, cobalt, or copper, can have increased toughness such as light resistance, water resistance, and heat resistance and can be used.

The content of the dye contained in the light-shielding film of the present invention is, when the dye is used alone, 13 wt % or more and 50 wt % or less, preferably 13 wt % or more and 40 wt % or less. In general, when dye is used for dyeing, the dye content is 10 wt % or less. However, in order to obtain a light-shielding property having a high extinction coefficient of 0.03, a dye content of 13 wt % or more is necessary. Since the content of the dye is high, the dye may not be dissolved in a resin, but it is not a problem in the present invention. However, a dye content of higher than 50 wt % deteriorates the solvent resistance. Therefore, the content is usually 50 wt % or less.

The inorganic black particles that have a d-line refractive index of 2.2 or more and 3.5 or less and give an extinction coefficient of 0.03 or more and 0.15 or less when they are contained in a light-shielding film may be contained in the light-shielding film of the present invention as a single kind of particles or two or more kinds of particles. Examples of the material for the inorganic black particles include TiN, titania covered with carbon black, titania covered with titanium black, zirconia covered with carbon black, and zirconia covered with titanium black.

The inorganic black particles of the present invention can have an average particle diameter of 10 nm or more and 100 nm or less, preferably 10 nm or more and 20 nm or less, and the content of particles having a particle diameter of 100 nm or more can be 1% or less. The inorganic black particles may have a smaller average particle diameter, but it is difficult to actually disperse particles having a particle diameter of 10 nm or less. On the other hand, if the average particle diameter of the inorganic black particles is 100 nm or more, scattering occurs to deteriorate the inner-surface reflection. In addition, if the content of particles having a diameter of 100 nm or more is higher than 1% of the inorganic black particles, scattering occurs to deteriorate the inner-surface reflection.

When the inorganic black particles are made of TiN alone, the content thereof can be 12 wt % or more and 45 wt % or less. If the TiN content is 12 wt % or less, the refractive index is not sufficiently increased, resulting in deterioration in the inner-surface reflection, but if the TiN content is higher than 45 wt %, the adhesive property of the film is deteriorated.

When the inorganic black particles having a d-line refractive index of 2.2 or more and 3.5 or less are made of titania covered with carbon black or titanium black or zirconia covered with carbon black or titanium black alone, the content thereof can be 10 wt % or more and 45 wt % or less. If the content is 10 wt % or less, the refractive index is not sufficiently increased, resulting in deteriorate in the inner-surface reflection, but if the content is higher than 45 wt %, the adhesive property of the film is deteriorated.

A resin having good adhesiveness with a base material, for example, a lens can be used. In order to improve the refractive index of the film as a whole, a resin itself having a high refractive index can be used. Examples of the resin having a high refractive index and good adhesiveness with a lens include epoxy resins. Other examples of the resin include, but not limited to, urethane resins, acrylic resins, melamine resins, and vinylidene chloride polymers.

The content of the resin contained in the light-shielding film of the present invention can be 10 wt % or more and 60 wt % or less, preferably 15 wt % or more and 30 wt % or less, as a ratio by weight when the film is formed. If the resin content is 10 wt % or less, the durability of the film is disadvantageously reduced.

The light-shielding film of the present invention can contain, as a material for improving the refractive index of the light-shielding film, non-black particles having an average particle diameter of 100 nm or less and a refractive index (nd) of 2.2 or more. If all the materials for improving the refractive index are black particles, the degree of blackness cannot be controlled. However, in order to control the degree of blackness, a small number of black particles having a refractive index (nd) of 2.2 or more may be contained in the light-shielding film. When the refractive index of the non-black particles is lower than 2.2, the refractive index of the light-shielding film cannot be sufficiently increased. Here, the particle diameters of the non-black particles are those of actual sizes of the particles present in the light-shielding film, that is, when the non-black particles are aggregated, the size is that of the aggregate. On this occasion, all the non-black particles can have particle diameters of 100 nm or less and can be uniformly dispersed. Even if the average particle diameter is small, if aggregated particles or coarse particles larger than 100 nm are contained, scattering occurs to reflect the refracted light that has entered the light-shielding film from the lens side, without the light-shielding film does not absorb the light. Examples of the non-black particles satisfying these properties include, but not limited to, nano-dispersed titania, zirconia, alumina, yttria, or ceria fine particles. The non-black particles can be titania, zirconia, or a mixture thereof. Furthermore, coal tar having a high refractive index may be used as a material for improving the refractive index.

The light-shielding film for optical element of the present invention may contain particles of a surface reflection preventing agent such as silica, quartz, or sericite. When the light-shielding film contains transparent fine particles of, for example, silica, quartz, or sericite, it is possible to form wrinkles or asperities on the surface, resulting in a decrease in reflection at the interface between the film and air. The content of other components contained in the light-shielding film of the present invention can be 0.1 wt % or more and 30 wt % or less, preferably 10 wt % or more and 20 wt % or less as a ratio by weight in the film.

Process of Producing Light-Shielding Film for Optical Element

The light-shielding film for optical element of the present invention is obtained by hardening a light-shielding coating for optical element.

The light-shielding coating for optical element contains at least a colorant, a resin, and a refractive-index-improving material. The light-shielding coating may further contain an additional component as long as the effects of the present invention are not impaired.

The light-shielding coating for optical element is obtained by dispersing the colorant, the resin, and the refractive-index-improving material by an appropriate mixing and dispersing process. Examples of the mixing and dispersing process include, but not limited to, collision dispersion, planetary rotation, and mixing/dispersing using a roll coater or a mixer.

The colorant can have high compatibility with a solvent and excellent toughness such as light resistance, water resistance, and heat resistance. An example such a colorant is azo dye containing chromium.

The non-black particles having an average particle diameter of 100 nm or less and a refractive index (nd) of 2.2 or more, which is an example of the refractive-index-improving material, may be a commercially available one. Examples of the process of producing slurry include a method of dispersing nano-fine particles with a bead mill or collision dispersion apparatus and a sol-gel method. In the slurry production, an appropriate surface treating agent or dispersant may be used.

The resin can have a high refractive index and high adhesiveness to a base material, such as a lens. An example of the resin is an epoxy resin.

Any solvent that can disperse the pigment and the refractive-index-improving material particles and can dissolve the dye can be used. Examples of the solvent include, but not limited to, toluene, hexane, cyclohexane, xylene, 1-butanol, butyl acetate, ethyl acetate, methyl isobutyl ketone (MIBK), and propylene glycol monomethyl ether (PGME).

The light-shielding coating may further contain additives, such as a hardener for hardening the resin, a coupling agent, a dispersant, an antiseptic agent, an antioxidant, and an antifungal agent, as additional components.

The optical element of the present invention is characterized by having the light-shielding film for optical element described above. Examples of the optical element include cameras, binoculars, microscopes, semiconductor exposure apparatuses, cameras for mobile phones, and broadcast equipment.

EXAMPLES

Preferred examples of the present invention will be described below.

Examples 1 to 24

Preparation of light-shielding coatings for optical element according to Examples 1 to 24, production of light-shielding films for optical element, and evaluation of optical properties were conducted as follows.

Preparation of Light-Shielding Coating for Optical Element

Tables 1 to 6 show resins, dyes, black pigments, non-black particles, solvents, coupling agents, hardeners, and their mixing ratios constituting light-shielding coatings for optical element A, B, C, D, E, F, G, H, I, J, K, L, M, N, O, R, S, T, U, V, W, X, Y, and AD. Light-shielding coating and light-shielding film for optical element A was used in Example 1; light-shielding coating and light-shielding film for optical element B was used in Example 2; light-shielding coating and light-shielding film for optical element C was used in Example 3; light-shielding coating and light-shielding film for optical element D was used in Example 4; light-shielding coating and light-shielding film for optical element E was used in Example 5; light-shielding coating and light-shielding film for optical element F was used in Example 6; light-shielding coating and light-shielding film for optical element G was used in Example 7; light-shielding coating and light-shielding film for optical element H was used in Example 8; light-shielding coating and light-shielding film for optical element I was used in Example 9; light-shielding coating and light-shielding film for optical element J was used in Example 10; light-shielding coating and light-shielding film for optical element K was used in Example 11; light-shielding coating and light-shielding film for optical element L was used in Example 12; light-shielding coating and light-shielding film for optical element M was used in Example 13; light-shielding coating and light-shielding film for optical element N was used in Example 14; light-shielding coating and light-shielding film for optical element O was used in Example 15; light-shielding coating and light-shielding film for optical element R was used in Example 16; light-shielding coating and light-shielding film for optical element S was used in Example 17; light-shielding coating and light-shielding film for optical element T was used in Example 18; light-shielding coating and light-shielding film for optical element U was used in Example 19; light-shielding coating and light-shielding film for optical element V was used in Example 20; light-shielding coating and light-shielding film for optical element W was used in Example 21; light-shielding coating and light-shielding film for optical element X was used in Example 22; light-shielding coating and light-shielding film for optical element Y was used in Example 23; and light-shielding coating and light-shielding film for optical element AD was used in Example 24.

The process of preparing the light-shielding coating for optical element will be described in detail using the light-shielding coating for optical element A as an example. First, an epoxy resin (4 g, Epicoat 828: Japan Epoxy Resins), a black dye (4 g), a red dye (2.9 g), a yellow dye (0.375 g), titania (2 g, ND139: Teica) serving as non-black particles, a solvent (24 g, propylene glycol monomethyl ether: Kishida Chemical), and a coupling agent (1.2 g, KBM-403: Shin-Etsu Chemical) were weighed and placed in a ball mill pot. Subsequently, five magnetic balls each having a diameter of 20 mm were put in the ball mill pot. The ball mill pot containing weighed coating components and the magnetic balls was set to a roll coater, followed by stirring at 66 rpm for 72 hours to obtain a light-shielding coating for optical element.

The dyes used were as follows.

The black dye was selected from VALIFAST BLACK 1821 (Orient Chemical), VALRFAST BLACK 3810 (Orient Chemical), Oil Black HBB (Orient Chemical), and Aizen Spilon Black MHS-Liquid (Hodogaya Chemical).

The red dye was selected from VALIFAST RED 3320 (Orient Chemical) and Aizen Spilon Red BEH S-Liquid (Hodogaya Chemical).

The yellow dye was selected from OIL YELLOW 129, VALIFAST YELLOW 3108, and Aizen Spilon Yellow RH S-Liquid (Hodogaya Chemical).

Production of Light-Shielding Film for Optical Element

A light-shielding film was formed from the light-shielding coating. A hardener (4 g, Adeca hardener EH551CH: Adeca) was added to the total amount of the light-shielding coating for optical element, and the mixture was stirred with a roll coater at 66 rpm for 30 minutes.

The resulting light-shielding coating for optical element/hardener solution was applied onto a prism for evaluation at a thickness of 2 μm, followed by drying at room temperature for 60 minutes. The light-shielding coating for optical element after the drying was hardened at 80° C. for 120 minutes in a heating furnace to obtain a light-shielding film for optical element.

Evaluation of Optical Properties

Method of Measuring Average Extinction Coefficient

A sample for measuring average extinction coefficient was prepared by forming a light-shielding film for optical element on a flat glass plate 20 mm in width, 50 mm in length, and 1 mm in thickness. The light-shielding film for optical element was formed on the upper surface of the flat glass plate so as to have a thickness of 1 μm. Then, transmittance was measured with a spectrometer (U-4000: Hitachi High-Technologies). The sample having the light-shielding film for measuring extinction coefficient was set to the spectrometer, and transmittance was measured at 1-nm intervals for visible light having wavelengths ranging from 400 to 700 nm, defining the transmittance of the flat glass plate as 100%. The average transmittance of the extinction-coefficient-measuring sample for the light having wavelengths ranging from 400 to 700 nm was calculated by dividing transmittance for each of the wavelengths ranging 400 to 700 nm by 300, which is the number of measurement points.

The extinction coefficient was calculated by the following Equations (3), (4), and (5) using the average transmittance I measured with the spectrometer. The optical density (OD) shown by Equation (3) represents absorbance and is a value obtained by taking −log of the value calculated by dividing the average transmittance I by the transmittance $I_0$ of the flat glass plate (100%). The absorbance coefficient α shown by Equation (4) represents the quantity of absorbed light per unit length, obtained by dividing the absorbance OD by the thickness L of the light-shielding film. The extinction coefficient k shown by Equation (5) is a value obtained by multiplying the absorbance coefficient α by a wavelength λ for nondimensionalization.

$$OD = -\log(I/I_0) \quad \text{Equation (3)}$$

$$\alpha = 2.303 \times OD/L \quad \text{Equation (4)}$$

$$k = \alpha \times \lambda / 4\pi \quad \text{Equation (5)}$$

Method of Measuring Inner-Surface Reflectance

Figure 4A:
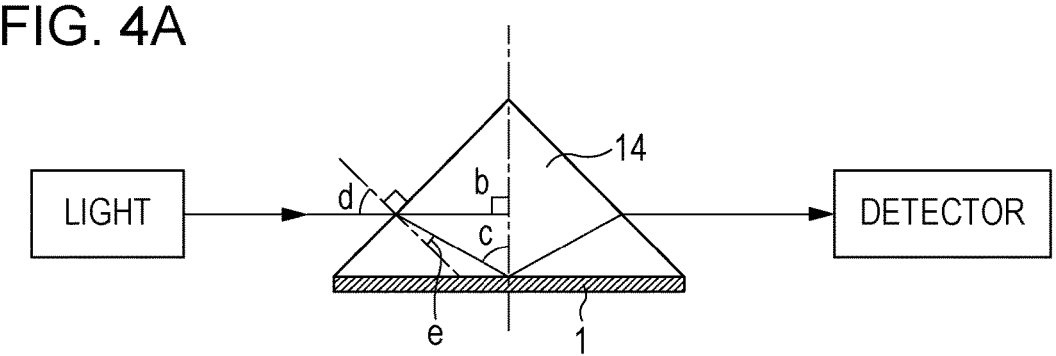
FIG. 4A is a schematic view illustrating a method of measuring inner-surface reflectance of a trigonal prism.
Figure 4B:
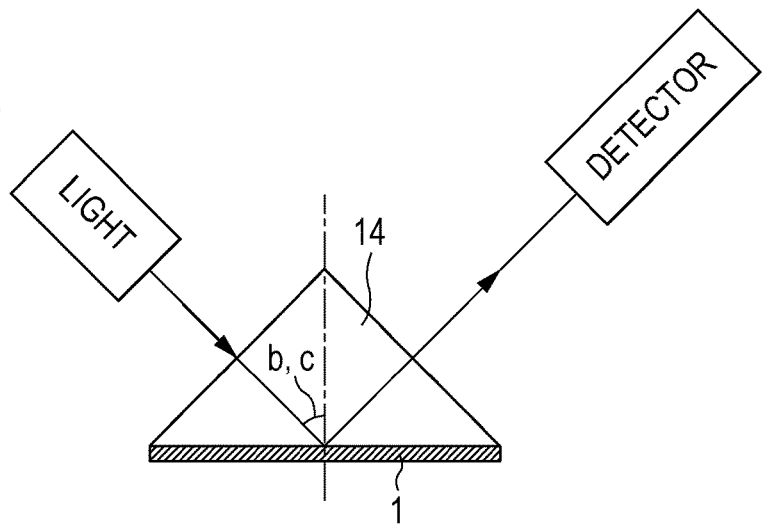
FIG. 4B is a schematic view illustrating the method of measuring inner-surface reflectance of the trigonal prism.
Figure 4C:
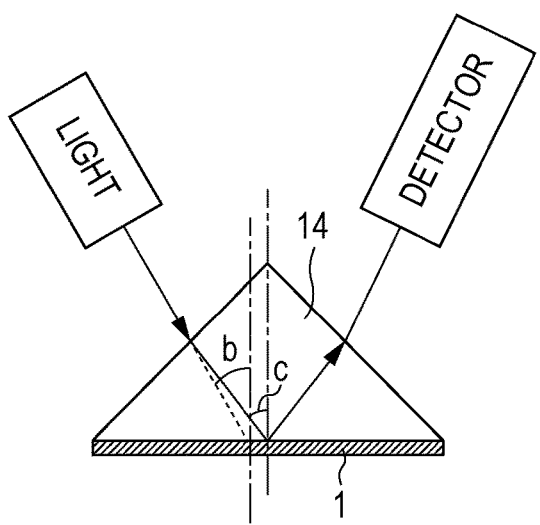
FIG. 4C is a schematic view illustrating the method of measuring inner-surface reflectance of the trigonal prism.

The inner-surface reflectance was measured using an ASP spectrometer (ASP-32: Bunko Keiki) as shown in FIGS. 4A to 4C. As the sample for the measurement, a trigonal prism 14 made of S-LAH53 (nd=1.805) and having a size in which the sides forming a right angle therebetween were each 30 mm and thickness was 10 mm was used.

FIG. 4A is a schematic view illustrating a method of measuring inner-surface reflectance when the incident angle b to the trigonal prism 14 is 90°. First, a method using the ASP spectrometer will be described with reference to FIG. 4A. Since the ASP spectrometer can freely change the angle between the sample and the detector, inner-surface reflectance can be measured fro each incident angle. The light emitted from the ASP spectrometer enters the trigonal prism 14 at an incident angle b of 90°. On this occasion, refraction of light occurs due to the difference in refractive indices of air and the prism. The incident angle c after the refraction is 68.13°. The angle e, after the refraction, to the incident angle d is calculated by the following Equation (6):

$$n = \sin d / \sin e \quad \text{Equation (6)}$$

The incident angle c was also calculated from the angle e after the refraction.

Subsequently, the light refracted by the trigonal prism 14 strikes the bottom surface of the trigonal prism 14 and is reflected to the outside of the trigonal prism 14. The intensity of this reflected light was detected over the visible light region, from 400 to 700 nm, with a detector. The background was determined using a trigonal prism 14 having a mirror bottom to which no film was applied. The inner-surface reflectance when the light-shielding film for optical element was applied to the brushed bottom of a trigonal prism 14 was measured. The inner-surface reflectance values shown in Tables 7 to 12 are averages of the results obtained by measuring inner-surface reflectance at 1-nm intervals for light having wavelengths ranging from 400 to 700 nm.

Similarly, FIG. 4B is a schematic view illustrating a method of measuring inner-surface reflectance when the incident angle b to the trigonal prism 14 was 45°. When the incident angle b to the trigonal prism 14 was 45°, the incident angle c after the refraction was 45° without change.

Similarly, FIG. 4C is a schematic view illustrating a method of measuring inner-surface reflectance when the incident angle b to the trigonal prism 14 was 30°. When the incident angle b to the trigonal prism 14 was 30°, the incident angle c after the refraction was 36.73°.

From correlation with the results of incorporation into mirror-barrel tests, a light-shielding film can be determined to have a satisfactory inner-surface reflectance when the inner-surface reflectance at an incident angle of 68.13° is 1% or less, the inner-surface reflectance at an incident angle of 45° is 0.07% or less, and the inner-surface reflectance at an incident angle of 36.73° is 0.05% or less.

Method of Measuring Degree of Blackness

The degree of blackness was determined by measuring transmittance for light having wavelengths from 400 to 700 nm using a spectrophotometer and substituting a minimum transmittance and a maximum transmittance in the results measured for the light having wavelengths from 400 to 700 nm into the following Equation (7) to calculate the ratio thereof.

$$\text{Degree of blackness} = (\text{minimum transmittance}) / (\text{maximum transmittance}) \quad \text{Equation (7)}$$

The sample for measuring the degree of blackness was prepared by forming a light-shielding film for optical element on a flat glass plate 20 mm in width, 50 mm in length, and 1 mm in thickness. The light-shielding film for optical element was formed on the upper surface of the flat glass plate so as to have a thickness of 1 μm. In general, a degree of blackness of 0.7 or more is satisfactory.

Method of Evaluating Appearance

Figure 5:
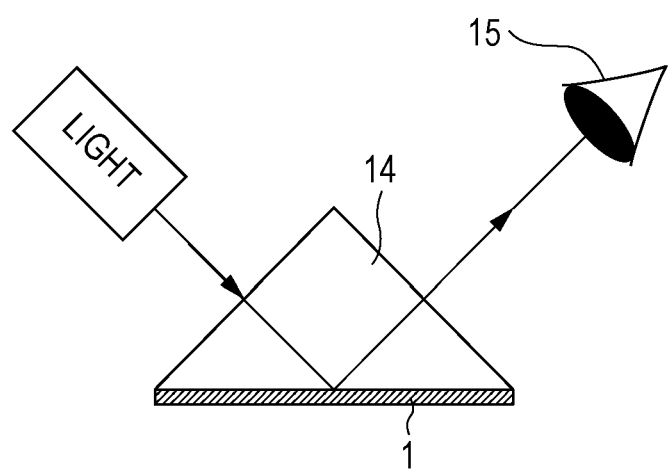
FIG. 5 is a schematic view illustrating a method of evaluating appearance of a trigonal prism.

The evaluation of appearance was performed by irradiation with light of 60 W from an irradiator, as shown in FIG. 5. As the sample for measurement, a trigonal prism 14 made of S-LAH53 (nd=1.805) and having a size in which the sides forming a right angle therebetween were each 30 mm and thickness was 10 mm was used. The light-shielding film was formed on the bottom of the trigonal prism 14, and the bottom was irradiated with light. The reflected light was visually observed by 15 inspectors. Roughness and color tone were evaluated as observation items.

Performance in the State Incorporated in Lens Barrel

The light-shielding film for optical element was formed on a telescopic lens, and the lens was incorporated into a lens barrel. The telescopic lens provided with the light-shielding film for optical element of the present invention was incorporated into a camera, and shooting was performed using the camera. The shot images were displayed for visually inspecting occurrence of flare and ghost.

TABLE 1

| | | | Light-shielding coating and film for optical element: A | Light-shielding coating and film for optical element: B | Light-shielding coating and film for optical element: C | Light-shielding coating and film for optical element: D |
|---|---|---|---|---|---|---|
| Light-shielding coating for optical element | Resin | material | epoxy | epoxy | epoxy | epoxy |
| | | content (g) | 4 | 4 | 4 | 4 |
| | Dye | material | azo dye | azo dye | azo dye | azo dye |
| | | model No. | (1)dye black (2)dye red (3)dye yellow | (1)dye black (2)dye red (3)dye yellow | (1)dye black (2)dye red (3)dye yellow | (1)dye black (2)dye red (3)dye yellow |
| | | content (g) | (1)4 (2)2.9 (3)0.375 | (1)6 (2)4.35 (3)0.562 | (1)4 (2)2.9 (3)0.375 | (1)4 (2)2.9 (3)0.375 |
| | | total dye content (g) | 7.275 | 10.912 | 7.275 | 7.275 |
| | Black pigment | material | — | — | carbon black | carbon black |
| | | particle diameter (μm): after aggregation | — | — | 0.1 | 10 |
| | | content (g) | 0 | 0 | 2 | 2 |

TABLE 1-continued

|  |  |  | Light-shielding coating and film for optical element: A | Light-shielding coating and film for optical element: B | Light-shielding coating and film for optical element: C | Light-shielding coating and film for optical element: D |
|---|---|---|---|---|---|---|
|  | Non-black particle | material | titania (dispersed in propylene glycol monomethyl ether, solid content: 25 wt %) | titania (dispersed in propylene glycol monomethyl ether, solid content: 25 wt %) | titania (dispersed in propylene glycol monomethyl ether, solid content: 25 wt %) | titania (dispersed in propylene glycol monomethyl ether, solid content: 25 wt %) |
|  |  | particle diameter (nm) | 20 | 20 | 20 | 20 |
|  |  | content (g): solid content weight | 2 | 2 | 2 | 2 |
|  | Solvent | material | propylene glycol monomethyl ether | propylene glycol monomethyl ether | propylene glycol monomethyl ether | propylene glycol monomethyl ether |
|  |  | content (g) | 24 | 24 | 24 | 24 |
|  | Coupling agent | material | epoxy-based silane coupling agent | epoxy-based silane coupling agent | epoxy-based silane coupling agent | epoxy-based silane coupling agent |
|  |  | content (g) | 1.2 | 1.2 | 1.2 | 1.2 |
|  | Surface-reflection inhibitor | material | — | — | — | — |
|  |  | content (g) | — | — | — | — |
|  |  | total content (g) | 0 | 0 | 0 | 0 |
|  | Hardener | material | amine base | amine base | amine base | amine base |
|  |  | content (g) | 4 | 4 | 4 | 4 |
| Light-shielding film for optical element | Thickness (μm) | dye content ratio (%) | 39.4 | 49.3 | 35.5 | 35.5 |
|  |  |  | 5 | 5 | 5 | 5 |

TABLE 2

|  |  |  | Light-shielding coating and film for optical element: E | Light-shielding coating and film for optical element: F | Light-shielding coating and film for optical element: G | Light-shielding coating and film for optical element: H |
|---|---|---|---|---|---|---|
| Light-shielding coating for optical element | Resin | material | epoxy | epoxy | epoxy | epoxy |
|  |  | content (g) | 4 | 4 | 4 | 4 |
|  | Dye | material model No. | azo dye (1)dye black (2)dye red (3)dye yellow | azo dye (1)dye black (2)dye red (3)dye yellow | azo dye (1)dye black (2)dye red (3)dye yellow | azo dye (1)dye black (2)dye red (3)dye yellow |
|  |  | content (g) | (1)4 (2)2.9 (3)0.375 | (1)4 (2)2.9 (3)0.375 | (1)4 (2)2.9 (3)0.375 | (1)9 (2)6.5 (3)0.84 |
|  |  | total dye content (g) | 7.275 | 7.275 | 7.275 | 16.34 |
|  | Black pigment | material | Cu—Fe—Mn complex oxide | Ti black | Copper oxide | — |
|  |  | particle diameter (μm): after aggregation | 0.1 | 0.2 | 0.2 | — |
|  |  | content (g) | 2 | 2 | 2 | 0 |
|  | Non-black particle | material | titania (dispersed in propylene glycol monomethyl ether, solid content: 25 wt %) | titania (dispersed in propylene glycol monomethyl ether, solid content: 25 wt %) | titania (dispersed in propylene glycol monomethyl ether, solid content: 25 wt %) | titania (dispersed in propylene glycol monomethyl ether, solid content: 25 wt %) |
|  |  | particle diameter (nm) | 20 | 20 | 20 | 20 |
|  |  | content (g): solid content weight | 2 | 2 | 2 | 2 |
|  | Solvent | material | propylene glycol monomethyl ether | propylene glycol monomethyl ether | propylene glycol monomethyl ether | propylene glycol monomethyl ether |
|  |  | content (g) | 24 | 24 | 24 | 24 |
|  | Coupling agent | material | epoxy-based silane coupling agent | epoxy-based silane coupling agent | epoxy-based silane coupling agent | epoxy-based silane coupling agent |
|  |  | content (g) | 1.2 | 1.2 | 1.2 | 1.2 |
|  | Surface-reflection inhibitor | material | — | — | — | — |
|  |  | content (g) | — | — | — | — |
|  |  | total content (g) | 0 | 0 | 0 | 0 |
|  | Hardener | material | amine base | amine base | amine base | amine base |
|  |  | content (g) | 4 | 4 | 4 | 4 |

TABLE 2-continued

|  |  | Light-shielding coating and film for optical element: E | Light-shielding coating and film for optical element: F | Light-shielding coating and film for optical element: G | Light-shielding coating and film for optical element: H |
| --- | --- | --- | --- | --- | --- |
| Light-shielding film for optical element | dye content ratio (%) | 35.5 | 35.5 | 35.5 | 59.3 |
|  | Thickness (μm) | 5 | 5 | 5 | 5 |

TABLE 3

|  |  |  | Light-shielding coating and film for optical element: I | Light-shielding coating and film for optical element: J | Light-shielding coating and film for optical element: K | Light-shielding coating and film for optical element: L |
| --- | --- | --- | --- | --- | --- | --- |
| Light-shielding coating for optical element | Resin | material | epoxy | epoxy | epoxy | epoxy |
|  |  | content (g) | 4 | 4 | 4 | 4 |
|  | Dye | material | azo dye | (1)-(3)azo dye (4)phthalocyanine dye | (1)-(3)azo dye (4)phthalocyanine dye | (1)-(3)azo dye (4)phthalocyanine dye |
|  |  | model No. | (1)dye black (2)dye red (3)dye yellow | (1)dye black (2)dye red (3)dye yellow (4)dye blue | (1)dye black (2)dye red (3)dye yellow (4)dye blue | (1)dye black (2)dye red (3)dye yellow (4)dye blue |
|  |  | content (g) | (1)4 (2)2.9 (3)0.375 | (1)0.55 (2)1.36 (3)0.55 (4)2.17 | (1)2.22 (2)5.52 (3)2.22 (4)8.82 | (1)0.55 (2)1.36 (3)0.55 (4)2.17 |
|  |  | total dye content (g) | 7.275 | 4.63 | 18.78 | 4.63 |
|  | Black pigment | material | iron oxide ($Fe_2O_3$) | — | — | — |
|  |  | particle diameter (μm): after aggregation | 0.1 | — | — | — |
|  |  | content (g) | 2 | 0 | 0 | 0 |
|  | Non-black particle | material | titania (dispersed in propylene glycol monomethyl ether, solid content: 25 wt %) | titania (dispersed in propylene glycol monomethyl ether, solid content: 25 wt %) | titania (dispersed in propylene glycol monomethyl ether, solid content: 25 wt %) | zirconia |
|  |  | particle diameter (nm) | 20 | 20 | 20 | 10 |
|  |  | content (g): solid content weight | 2 | 5 | 5 | 5 |
|  | Solvent | material | propylene glycol monomethyl ether | propylene glycol monomethyl ether | propylene glycol monomethyl ether | propylene glycol monomethyl ether |
|  |  | content (g) | 24 | 12 | 12 | 12 |
|  | Coupling agent | material | epoxy-based silane coupling agent | epoxy-based silane coupling agent | epoxy-based silane coupling agent | epoxy-based silane coupling agent |
|  |  | content (g) | 1.2 | 1.2 | 1.2 | 1.2 |
|  | Surface-reflection inhibitor | material | — | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz |
|  |  | content (g) | — | (1)1.6 (2)0.7 (3)0.8 (4)1.0 | (1)1.6 (2)0.7 (3)0.8 (4)1.0 | (1)1.6 (2)0.7 (3)0.8 (4)1.0 |
|  |  | total content (g) | 0 | 4.1 | 4.1 | 4.1 |
|  | Hardener | material | amine base | amine base | amine base | amine base |
|  |  | content (g) | 4 | 4 | 4 | 4 |
| Light-shielding film for optical element | dye content ratio (%) | | 35.5 | 20.2 | 50.6 | 20.2 |
|  | Thickness (μm) | | 5 | 5 | 5 | 5 |

TABLE 4

|  |  |  | Light-shielding coating and film for optical element: M | Light-shielding coating and film for optical element: N | Light-shielding coating and film for optical element: O |
|---|---|---|---|---|---|
| Light-shielding coating for optical element | Resin | material | epoxy | epoxy | epoxy |
|  |  | content (g) | 4 | 4 | 4 |
|  | Dye | material | (1)-(3)azo dye (4)phthalocyanine dye | (1)-(3)azo dye (4)phthalocyanine dye | (1)-(3)azo dye (4)phthalocyanine dye |
|  |  | model No. | (1)dye black (2)dye red (3)dye yellow (4)dye blue | (1)dye black (2)dye red (3)dye yellow (4)dye blue | (1)dye black (2)dye red (3)dye yellow (4)dye blue |
|  |  | content (g) | (1)0.55 (2)1.36 (3)0.55 (4)2.17 | (1)0.55 (2)1.36 (3)0.55 (4)2.17 | (1)0.55 (2)1.36 (3)0.55 (4)2.17 |
|  |  | total dye content (g) | 4.63 | 4.63 | 4.63 |
|  | Black pigment | material | — | — | — |
|  |  | particle diameter (μm): after aggregation | — | — | — |
|  |  | content (g) | 0 | 0 | 0 |
|  | Non-black particle | material | titania (dispersed in propylene glycol monomethyl ether, solid content: 25 wt %) | titania (dispersed in propylene glycol monomethyl ether, solid content: 25 wt %) | titania (dispersed in propylene glycol monomethyl ether, solid content: 25 wt %) |
|  |  | particle diameter (nm) | 20 | 20 | 20 |
|  |  | content (g): solid content weight | 5 | 5 | 5 |
|  | Solvent | material | propylene glycol monomethyl ether | propylene glycol monomethyl ether | propylene glycol monomethyl ether |
|  |  | content (g) | 12 | 12 | 12 |
|  | Coupling agent | material | epoxy-based silane coupling agent | epoxy-based silane coupling agent | epoxy-based silane coupling agent |
|  |  | content (g) | 1.2 | 1.2 | 1.2 |
|  | Surface-reflection inhibitor | material | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz |
|  |  | content (g) | (1)1.6 (2)0.7 (3)0.8 (4)1.0 | (1)1.6 (2)0.7 (3)0.8 (4)1.0 | (1)1.6 (2)0.7 (3)0.8 (4)1.0 |
|  |  | total content (g) | 4.1 | 4.1 | 4.1 |
|  | Hardener | material | amine base | amine base | amine base |
|  |  | content (g) | 4 | 4 | 4 |
| Light-shielding film for optical element |  | dye content ratio (%) | 20.2 | 20.2 | 20.2 |
|  | Thickness (μm) |  | 2 | 10 | 50 |

TABLE 5

|  |  |  | Light-shielding coating and film for optical element: R | Light-shielding coating and film for optical element: S | Light-shielding coating and film for optical element: T | Light-shielding coating and film for optical element: U |
|---|---|---|---|---|---|---|
| Light-Shielding coating for optical element | Resin | material | epoxy | epoxy | epoxy | epoxy |
|  |  | content (g) | 4 | 4 | 4 | 4 |
|  | Inorganic black particle with a d-line refractive index of 2.2 to 3.5 | material | carbon black-coated titania | carbon black-coated zirconia | titanium black-coated titania | titanium black-coated zirconia |
|  |  | d-line refractive index | 2.5 | 2.2 | 2.5 | 2.2 |
|  |  | particle diameter (nm) | 20 | 20 | 20 | 20 |
|  |  | content (g): solid content weight | 1.5 | 10.9 | 1.5 | 1.5 |
|  | Solvent | material | propylene glycol monomethyl ether | propylene glycol monomethyl ether | propylene glycol monomethyl ether | propylene glycol monomethyl ether |
|  |  | content (g) | 24 | 24 | 24 | 24 |

TABLE 5-continued

|  |  |  | Light-shielding coating and film for optical element: R | Light-shielding coating and film for optical element: S | Light-shielding coating and film for optical element: T | Light-shielding coating and film for optical element: U |
| --- | --- | --- | --- | --- | --- | --- |
|  | Coupling agent | material | epoxy-based silane coupling agent | epoxy-based silane coupling agent | epoxy-based silane coupling agent | epoxy-based silane coupling agent |
|  |  | content (g) | 1.2 | 1.2 | 1.2 | 1.2 |
|  | Surface-reflection inhibitor | material | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz |
|  |  | content (g) | (1)1.6 (2)0.7 (3)0.8 (4)1.0 | (1)1.6 (2)0.7 (3)0.8 (4)1.0 | (1)1.6 (2)0.7 (3)0.8 (4)1.0 | (1)1.6 (2)0.7 (3)0.8 (4)1.0 |
|  |  | total content (g) | 4.1 | 4.1 | 4.1 | 4.1 |
|  | Hardener | material | amine base | amine base | amine base | amine base |
|  |  | content (g) | 4 | 4 | 4 | 4 |
| Light-shielding film for optical element | Content (%) of inorganic black particle with a d-line refractive index of 2.2 to 3.5 |  | 10 | 45 | 10 | 10 |
|  | Thickness (μm) |  | 5 | 5 | 5 | 5 |

TABLE 6

|  |  |  | Light-shielding coating and film for optical element: V | Light-shielding coating and film for optical element: W | Light-shielding coating and film for optical element: X | Light-shielding coating and film for optical element: Y |
| --- | --- | --- | --- | --- | --- | --- |
| Light-shielding coating for optical element | Resin | material | epoxy | epoxy | epoxy | epoxy |
|  |  | content (g) | 4 | 4 | 4 | 4 |
|  | Inorganic black particle with a d-line refractive index of 2.2 to 3.5 | material | TiN | TiN | TiN | TiN |
|  |  | d-line refractive index | 3.5 | 3.5 | 3.5 | 3.5 |
|  |  | particle diameter (nm) | 20 | 100 | 20 | 20 |
|  |  | content (g): solid content weight | 1.8 | 1.8 | 11 | 1.8 |
|  | Solvent | material | propylene glycol monomethyl ether | propylene glycol monomethyl ether | propylene glycol monomethyl ether | propylene glycol monomethyl ether |
|  |  | content (g) | 24 | 24 | 24 | 24 |
|  | Coupling agent | material | epoxy-based silane coupling agent | epoxy-based silane coupling agent | epoxy-based silane coupling agent | epoxy-based silane coupling agent |
|  |  | content (g) | 1.2 | 1.2 | 1.2 | 1.2 |
|  | Surface-reflection inhibitor | material | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz |
|  |  | content (g) | (1)1.6 (2)0.7 (3)0.8 (4)1.0 | (1)1.6 (2)0.7 (3)0.8 (4)1.0 | (1)1.6 (2)0.7 (3)0.8 (4)1.0 | (1)1.6 (2)0.7 (3)0.8 (4)1.5 |
|  |  | total content (g) | 4.1 | 4.1 | 4.1 | 4.1 |
|  | Hardener | material | amine base | amine base | amine base | amine base |
|  |  | content (g) | 4 | 4 | 4 | 4 |
| Light-shielding film for optical element | Content (%) of inorganic black particle with a d-line refractive index of 2.2 to 3.5 |  | 12 | 12 | 45 | 12 |
|  | Thickness (μm) |  | 5 | 5 | 5 | 5 |

TABLE 7

| | | | Light-shielding coating and film for optical element: AD |
|---|---|---|---|
| Light-shielding coating for optical element | Resin | material | epoxy |
| | | content (g) | 4 |
| | Dye | material model No. | azo dye (1)dye black (2)dye red (3)dye yellow (4)dye blue |
| | | content (g) | (1)0.202 (2)0.499 (3)0.202 (4)0.797 |
| | | total dye content (g) | 1.7 |
| | Black pigment | material | — |
| | | particle diameter (μm) | — |
| | | content (g) | 0 |
| | Non-black particle | material | titania (dispersed in propylene glycol monomethyl ether, solid content: 25 wt %) |
| | | particle diameter (nm) | 20 |
| | | content (g): solid content weight | 2 |
| | Solvent | material | propylene glycol monomethyl ether |
| | | content (g) | 24 |
| | Coupling agent | material | epoxy-based silane coupling agent |
| | | content (g) | 1.9 |
| | Surface-reflection inhibitor | material | — |
| | | content (g) | — |
| | | total content (g) | 1.4 |
| | Hardener | material | amine base |
| | | content (g) | 1.63 |
| Light-shielding film for optical element | | dye content (%) | 13.0 |
| | Thickness (μm) | | 5 |

(Note 1) Appearance
Excellent: no problem in color tone, and no roughness
Good: lens, itself, having a slightly deteriorated color tone that is not recognized in the state that the lens is incorporated in a lens barrel or having roughness that is not recognized in the state that the lens is incorporated in a lens barrel
(Note 2) Performance in the State Incorporated in Lens Barrel
Excellent: no occurrence of flare and ghost
Good: no occurrence of flare and ghost, but there is a chance of defectiveness that the lens is not incorporated into a lens barrel
Poor: occurrence of flare and ghost
Evaluation Results Light-shielding coatings and films for optical element A, B, C, D, E, F, G, H, I, J, K, L, M, N, O, R, S, T, U, V, W, X, Y, and AD, their inner-surface reflectance, degree of blackness, appearance, and performance in the state incorporated in lens barrel were evaluated by the above-described methods.

As the measurement results, the average extinction coefficient k was 0.03 or more and 0.15 or less. It is desirable that the inner-surface reflectance at an incident angle of 36.73° is 0.05% or less, the inner-surface reflectance at an incident angle of 45° is 0.07% or less, and the inner-surface reflectance at an incident angle of 68.13° is 1% or less. In addition, it is desirable that the degree of blackness is 0.7 or more.

Each physical property of light-shielding coating and light-shielding film for optical element A was measured and is shown as Example 1 in Table 8. The average extinction coefficient k was calculated by Equations (3), (4), and (5) as below. First, the average I (40.1%) of the measured values of transmittance for light having wavelengths from 400 to 700 nm was substituted into Equation (3) to obtain an OD value of 0.40. Then, the values, OD=0.40 and L=1 (μm), were substituted into Equation (4) to obtain an α value of 0.91, and the resulting value, α=0.91, was substituted into Equation (5) to calculate an average extinction coefficient k of 0.04. The inner-surface reflectance at an incident angle of 68.13° was 0.64%, the inner-surface reflectance at an incident angle of 45° was 0.0052%, and the inner-surface reflectance at an incident angle of 36.73° was 0.032%. Regarding the degree of blackness, in the wavelength range from 400 to 700 nm, the minimum transmittance was 41.8% at 687 nm, and the maximum transmittance was 59.8% at 596 nm. These values were substituted into Equation (7) to obtain a degree of blackness of 0.7. The appearance was satisfactory in both roughness and color tone. Furthermore, no flare and ghost were observed in evaluation of an image shot by the camera in which a telescopic lens provided with light-shielding film A was incorporated.

Each physical property of light-shielding coating and light-shielding film B, in which the dye content was about 50% unlike Example 1, is shown as Example 2 in Table 8. The average extinction coefficient k, the inner-surface reflectance at incident angles of 36.73°, 45°, and 68.13°, and the degree of blackness were all satisfactory. In addition, the appearance was satisfactory in both roughness and color tone. Furthermore, no flare and ghost were observed in evaluation of an image shot by the camera in which a telescopic lens provided with light-shielding film B was incorporated.

Each physical property of light-shielding coating and light-shielding film C, in which dye and carbon black (Mitsubishi carbon black MA100) having a diameter, after dispersion, of 0.1 μm were contained unlike Example 1, is shown as Example 3 in Table 8. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film C was incorporated.

Each physical property of light-shielding coating and light-shielding film D, in which dye and carbon black (Mitsubishi carbon black MA100) having a diameter, after dispersion, of 10 μm were contained unlike Example 1, is shown as Example 4 in Table 8. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film D was incorporated.

Each physical property of light-shielding coating and light-shielding film E, in which dye and copper-manganese complex oxide (BLACK PIGMENT SLURRY: C. I. Kasei) serving as pigment were contained unlike Example 1, is shown as Example 5 in Table 9. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film E was incorporated.

Each physical property of light-shielding coating and light-shielding film F, in which dye and titanium black (13M: Mitsubishi Materials) serving as pigment were contained unlike Example 1, is shown as Example 6 in Table 9. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film F was incorporated.

Each physical property of light-shielding coating and light-shielding film G, in which dye and copper oxide (Nisshin Engineering) serving as pigment were contained unlike Example 1, is shown as Example 7 in Table 9. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film G was incorporated.

Each physical property of light-shielding coating and light-shielding film H, in which the dye content was about 60% unlike Example 1, is shown as Example 8 in Table 9. The average extinction coefficient k, the inner-surface reflectance at incident angles of 36.73°, 45°, and 68.13°, and the degree of blackness were all satisfactory. In addition, the appearance was satisfactory in both roughness and color tone. Furthermore, no flare and ghost were observed in evaluation of an image shot by the camera in which a telescopic lens provided with light-shielding film H was incorporated. However, durability of light-shielding film A was superior to that of light-shielding film H.

Each physical property of light-shielding coating and light-shielding film I, in which dye and iron oxide ($Fe_2O_3$: Sakai Chemical Industry) serving as pigment were contained unlike Example 1, is shown as Example 9 in Table 10. Iron oxide is reddish, therefore, the average extinction coefficient k and the inner-surface reflectance at incident angles of 36.73°, 45°, and 68.13° were satisfactory, but the degree of blackness was low, i.e., 0.6. Regarding the appearance, though roughness was observed, color tone was satisfactory. Furthermore, no flare and ghost were observed in evaluation of an image shot by the camera in which a telescopic lens provided with light-shielding film I was incorporated.

Each physical property of light-shielding coating and light-shielding film J, in which the dye content was 20 wt %, the amount of the non-black particles was increased to 5 g, and a blue dye and a surface-reflection inhibitor were contained, is shown as Example 10 in Table 9. As the materials of the surface-reflection inhibitor, the followings were used: silica (hydrophilic) was hydrophilic Aerozil having an average particle diameter of about 10 nm (any of Aerozil 90, 150, 200, 300, and 380: Nippon Aerozil); silica (hydrophobic) was hydrophobic Aerozil having an average particle diameter of about 10 nm (any of Aerozil R972, R974, R104, R106, R202, R805, and R812: Nippon Aerozil); quartz was Crystallite having an average particle diameter of about 10 μm (any of A-1, A-A, VX-S2, VX-S, and 5X: Tatsumori); and sericite was Takara Mica M-101 (manufactured by Shiraishi Calcium Co., Ltd.) or Hikawa Mica Z20 (manufactured by Hikawa Kogyo Co., Ltd.) having an average particle diameter of about 10 μm. The blue dye used was any of the followings: VALIFAST BLUE 1605 (Orient Chemical), VALIFAST BLUE 2650 (Orient Chemical), VALIFAST BLUE 2620 (Orient Chemical), VALIFAST BLUE 2606 (Orient Chemical), and Aizen Victoria Pure Blue BOH (Hodogaya Chemical). As a result, the average extinction coefficient k was 0.03. Furthermore, the inner-surface reflectance at an incident angle of 36.73° was very good. In addition, the inner-surface reflectance at an incident angle of 68.13° was satisfactory. The appearance was satisfactory in both roughness and color tone. Furthermore, no flare and ghost were observed in evaluation of an image shot by the camera in which a telescopic lens provided with light-shielding film J was incorporated.

Each physical property of light-shielding coating and light-shielding film K, in which a surface-reflection inhibitor and a blue dye were contained and the dye content was about 50 wt % unlike Example 1, is shown as Example 11 in Table 10. The average extinction coefficient k, the inner-surface reflectance at incident angles of 36.73°, 45°, and 68.13°, and the degree of blackness were all satisfactory. In addition, the appearance was satisfactory in both roughness and color tone. Furthermore, no flare and ghost were observed in evaluation of an image shot by the camera in which a telescopic lens provided with light-shielding film K was incorporated.

Each physical property of light-shielding coating and light-shielding film L, in which a surface-reflection inhibitor and a blue dye were contained, and zirconia (Sumitomo Osaka Cement) was used as non-black particles unlike Example 1, is shown as Example 12 in Table 10. The average extinction coefficient k, the inner-surface reflectance at incident angles of 36.73°, 45°, and 68.13°, and the degree of blackness were all satisfactory. In addition, the appearance was satisfactory in both roughness and color tone. Furthermore, no flare and ghost were observed in evaluation of an image shot by the camera in which a telescopic lens provided with light-shielding film L was incorporated.

Each physical property of light-shielding coating and light-shielding film M, in which a surface-reflection inhibitor and a blue dye were contained, and the thickness was adjusted to 2 μm unlike Example 1, is shown as Example 13 in Table 11. The average extinction coefficient k, the inner-surface reflectance at incident angles of 36.73°, 45°, and 68.13°, and the degree of blackness were all satisfactory. In addition, the appearance was satisfactory in both roughness and color tone. Furthermore, no flare and ghost were observed in evaluation of an image shot by the camera in which a telescopic lens provided with light-shielding film M was incorporated.

Each physical property of light-shielding coating and light-shielding film N, in which a surface-reflection inhibitor and a blue dye were contained, and the thickness was adjusted to 10 μm unlike Example 1, is shown as Example 14 in Table 11. The average extinction coefficient k, the inner-surface reflectance at incident angles of 36.73°, 45°, and 68.13°, and the degree of blackness were all satisfactory. In addition, the appearance was satisfactory in both roughness and color tone. Furthermore, no flare and ghost were observed in evaluation of an image shot by the camera in which a telescopic lens provided with light-shielding film N was incorporated.

Each physical property of light-shielding coating and light-shielding film O, in which a surface-reflection inhibitor and a blue dye were contained, and the thickness was adjusted to 50 µm unlike Example 1, is shown as Example 15 in Table 11. The average extinction coefficient k, the inner-surface reflectance at incident angles of 36.73°, 45°, and 68.13°, and the degree of blackness were all satisfactory. In addition, the appearance was satisfactory in both roughness and color tone. Furthermore, no flare and ghost were observed in evaluation of an image shot by the camera in which a telescopic lens provided with light-shielding film O was incorporated. However, defective lenses that were not smoothly incorporated into lens barrels occurred.

Each physical property of light-shielding coating and light-shielding film R, in which 10 wt % of carbon black-coated titania having a particle diameter of 20 nm was contained in the colorant unlike Example 1, is shown as Example 16 in Table 11.

The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film R was incorporated.

Each physical property of light-shielding coating and light-shielding film S, in which 45 wt % of carbon black-coated zirconia having a particle diameter of 20 nm was contained in the colorant unlike Example 16, is shown as Example 17 in Table 12. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film S was incorporated.

Each physical property of light-shielding coating and light-shielding film T, in which 10 wt % of titanium black-coated titania having a particle diameter of 20 nm was contained in the colorant unlike Example 16, is shown as Example 18 in Table 12. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film T was incorporated.

Each physical property of light-shielding coating and light-shielding film U, in which 10 wt % of carbon black-coated zirconia having a particle diameter of 20 nm was contained in the colorant unlike Example 16, is shown as Example 19 in Table 12. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film U was incorporated.

Each physical property of light-shielding coating and light-shielding film V, in which 12 wt % of TiN having a particle diameter of 20 nm was contained in the colorant unlike Example 16, is shown as Example 20 in Table 13. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film V was incorporated.

Each physical property of light-shielding coating and light-shielding film W, in which 12 wt % of TiN having a particle diameter of 100 nm was contained in the colorant unlike Example 20, is shown as Example 21 in Table 13. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film W was incorporated.

Each physical property of light-shielding coating and light-shielding film X, in which 45 wt % of TiN having a particle diameter of 20 nm was contained in the colorant unlike Example 20, is shown as Example 22 in Table 13. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film X was incorporated.

Each physical property of light-shielding coating and light-shielding film Y, in which 12 wt % of TiN having a particle diameter of 110 nm was contained in the colorant unlike Example 17, is shown as Example 23 in Table 13. The average extinction coefficient k, the inner-surface reflectance at incident angles of 36.73°, 45°, and 68.13°, and the degree of blackness were all satisfactory. In addition, regarding the appearance, though roughness was observed, color tone was satisfactory. Furthermore, no flare and ghost were observed in evaluation of an image shot by the camera in which a telescopic lens provided with light-shielding film Y was incorporated.

Each physical property of light-shielding coating and light-shielding film AD, in which 13 wt % of a dye was contained in the colorant unlike Example 1, is shown as Example 24 in Table 14. The average extinction coefficient k, the inner-surface reflectance at incident angles of 36.73°, 45°, and 68.13°, and the degree of blackness were all satisfactory. Furthermore, no flare and ghost were observed in evaluation of an image shot by the camera in which a telescopic lens provided with light-shielding film Y was incorporated.

TABLE 8

|  |  |  | Example 1 | Example 2 | Example 3 | Example 4 |
|---|---|---|---|---|---|---|
| Evaluation of optical properties | Extinction coefficient | | 0.04 | 0.05 | 0.15 | 0.1 |
| | inner-surface reflectance(Ave. | incident angle after refraction: 68.13° | 0.64 | 0.62 | 0.67 | 0.65 |

TABLE 8-continued

|  |  | Example 1 | Example 2 | Example 3 | Example 4 |
|---|---|---|---|---|---|
| 400-700 nm %) | incident angle after refraction: 45° | 0.052 | 0.041 | 0.064 | 0.029 |
|  | incident angle after refraction: 36.73° | 0.032 | 0.026 | 0.048 | 0.029 |
| Degree of blackness |  | 0.70 | 0.70 | 0.90 | 0.90 |
| Appearance |  | excellent | excellent | good | good |
| Performance at fitting in lens barrel |  | excellent | excellent | excellent | excellent |

TABLE 9

|  |  |  | Example 5 | Example 6 | Example 7 | Example 8 |
|---|---|---|---|---|---|---|
| Evaluation of optical properties | Extinction coefficient |  | 0.09 | 0.05 | 0.04 | 0.06 |
|  | inner-surface reflectance(Ave. 400-700 nm %) | incident angle after refraction: 68.13° | 0.59 | 0.62 | 0.62 | 0.62 |
|  |  | incident angle after refraction: 45° | 0.021 | 0.032 | 0.040 | 0.041 |
|  |  | incident angle after refraction: 36.73° | 0.014 | 0.020 | 0.024 | 0.026 |
|  | Degree of blackness |  | 0.90 | 0.80 | 0.80 | 0.70 |
|  | Appearance |  | good | good | good | excellent |
|  | Performance at fitting in lens barrel |  | excellent | excellent | excellent | excellent |

TABLE 10

|  |  |  | Example 9 | Example 10 | Example 11 | Example 12 |
|---|---|---|---|---|---|---|
| Evaluation of optical properties | Extinction coefficient |  | 0.11 | 0.03 | 0.05 | 0.03 |
|  | inner-surface reflectance(Ave. 400-700 nm %) | incident angle after refraction: 68.13° | 0.66 | 0.26 | 0.27 | 0.9 |
|  |  | incident angle after refraction: 45° | 0.035 | 0.003 | ≤0.001 | 0.003 |
|  |  | incident angle after refraction: 36.73° | 0.033 | 0.002 | ≤0.001 | 0.002 |
|  | Degree of blackness |  | 0.60 | 0.8 | 0.8 | 0.7 |
|  | Appearance |  | good | excellent | excellent | excellent |
|  | Performance at fitting in lens barrel |  | excellent | excellent | excellent | excellent |

TABLE 11

|  |  |  | Example 13 | Example 14 | Example 15 |
|---|---|---|---|---|---|
| Evaluation of optical properties | Extinction coefficient |  | 0.03 | 0.03 | 0.03 |
|  | inner-surface reflectance(Ave. 400-700 nm %) | incident angle after refraction: 68.13° | 0.26 | 0.25 | 0.25 |
|  |  | incident angle after refraction: 45° | 0.04 | ≤0.001 | ≤0.001 |
|  |  | incident angle after refraction: 36.73° | 0.03 | ≤0.001 | ≤0.001 |
|  | Degree of blackness |  | 0.7 | 0.7 | 0.7 |
|  | Appearance |  | excellent | excellent | excellent |
|  | Performance at fitting in lens barrel |  | excellent | excellent | good |

TABLE 12

|  |  |  | Example 16 | Example 17 | Example 18 | Example 19 |
|---|---|---|---|---|---|---|
| Evaluation of optical properties | Extinction coefficient |  | 0.03 | 0.15 | 0.03 | 0.03 |
|  | inner-surface reflectance (Ave. | incident angle after refraction: 68.13° | 0.29 | 0.88 | 0.31 | 0.92 |

TABLE 12-continued

|  |  | Example 16 | Example 17 | Example 18 | Example 19 |
|---|---|---|---|---|---|
| 400-700 nm %) | incident angle after refraction: 45° | 0.03 | 0.04 | 0.03 | 0.03 |
|  | incident angle after refraction: 36.73° | 0.02 | 0.03 | 0.02 | 0.02 |
| Degree of blackness |  | 1 | 1 | 1 | 1 |
| Appearance |  | good | good | good | good |
| Performance at fitting in lens barrel |  | excellent | excellent | excellent | excellent |

TABLE 13

|  |  |  | Example 20 | Example 21 | Example 22 | Example 23 |
|---|---|---|---|---|---|---|
| Evaluation of optical properties | Extinction coefficient |  | 0.03 | 0.03 | 0.15 | 0.03 |
|  | inner-surface reflectance (Ave. 400-700 nm %) | incident angle after refraction: 68.13° | 0.18 | 0.21 | 0.11 | 0.2 |
|  |  | incident angle after refraction: 45° | 0.03 | 0.04 | 0.04 | 0.07 |
|  |  | incident angle after refraction: 36.73° | 0.02 | 0.03 | 0.03 | 0.05 |
|  | Degree of blackness |  | 1 | 1 | 1 | 1 |
|  | Appearance |  | good | good | good | good |
|  | Performance at fitting in lens barrel |  | excellent | excellent | excellent | excellent |

TABLE 14

|  |  | Example 24 |
|---|---|---|
| Extinction coefficient |  | 0.03 |
| inner-surface reflectance(Ave. 400-700 nm %) | incident angle after refraction: 68.13° | 0.42 |
|  | incident angle after refraction: 45° | 0.06 |
|  | incident angle after refraction: 36.73° | 0.04 |
| Degree of blackness |  | 0.8 |
| Appearance |  | good |
| Performance at fitting in lens barrel |  | excellent |

Comparative Examples 1 to 6

In Comparative Examples, preparation of light-shielding coatings for optical element, production of light-shielding films for optical element, and evaluation of optical properties were performed as in the above-described Examples 1 to 23, except the followings.

Tables 15 and 16 show resins, dyes, black pigments, non-black particles, solvents, coupling agents, and their mixing ratios constituting light-shielding coatings and films for optical element P, Q, Z, AA, AB, and AC.

Tables 17 and 18 show the results of optical property evaluation of light-shielding coatings and films for optical element P, Q, Z, AA, AB, and AC as Comparative Examples 1, 2, 3, 4, 5, and 6, respectively.

TABLE 15

|  |  |  | Light-shielding coating and film for optical element: P | Light-shielding coating and film for optical element: Q |
|---|---|---|---|---|
| Light-shielding coating for optical element | Resin | material | epoxy | epoxy |
|  |  | content (g) | 4 | 4 |
|  | Dye | material | azo dye | azo dye |
|  |  | model No. | (1)dye black (2)dye red (3)dye yellow (4)dye blue | (1)dye black (2)dye red (3)dye yellow (4)dye blue |
|  |  | content (g) | (1)0.148 (2)0.367 (3)0.148 (4)0.586 | (1)4 (2)2.9 (3)0.375 |
|  |  | total dye content (g) | 1.5 | 7.275 |
|  | Black pigment | material | — | carbon black |
|  |  | particle diameter (μm): after aggregation | — | 0.1 |
|  |  | content (g) | 0 | 3 |

TABLE 15-continued

|  |  |  | Light-shielding coating and film for optical element: P | Light-shielding coating and film for optical element: Q |
|---|---|---|---|---|
| | Non-black particle | material | titania (dispersed in propylene glycol monomethyl ether, solid content: 25 wt %) | titania (dispersed in propylene glycol monomethyl ether, solid content: 25 wt %) |
| | | particle diameter (nm) | 20 | 20 |
| | | content (g): solid content weight | 2 | 2 |
| | Solvent | material | propylene glycol monomethyl ether | propylene glycol monomethyl ether |
| | | content (g) | 24 | 24 |
| | Coupling agent | material | epoxy-based silane coupling agent | epoxy-based silane coupling agent |
| | | content (g) | 1.9 | 1.2 |
| | Surface-reflection inhibitor | material | — | — |
| | | content (g) | — | — |
| | | total content (g) | 1.4 | 0 |
| | Hardener | material | amine base | amine base |
| | | content (g) | 1.63 | 4 |
| Light-shielding film for optical element | | dye content ratio (%) | 12.0 | 33.9 |
| | Thickness (μm) | | 5 | 5 |

TABLE 16

|  |  |  | Light-shielding coating and film for optical element: Z | Light-shielding coating and film for optical element: AA | Light-shielding coating and film for optical element: AB | Light-shielding coating and film for optical element: AC |
|---|---|---|---|---|---|---|
| Light-shielding coating for optical element | Resin | material | epoxy | epoxy | epoxy | epoxy |
| | | content (g) | 4 | 4 | 4 | 4 |
| | Inorganic black particle with a d-line refractive index of 2.2 to 3.5 | material | TiN | TiN | TiN | TiN |
| | | d-line refractive index | 3.5 | 3.5 | 3.5 | 3.5 |
| | | particle diameter (nm) | 20 | 20 | 20 | 20 |
| | | content (g): solid content weight | 1.2 | 1.2 | 1.5 | 5 |
| | Solvent | material | propylene glycol monomethyl ether | propylene glycol monomethyl ether | propylene glycol monomethyl ether | propylene glycol monomethyl ether |
| | | content (g) | 24 | 24 | 24 | 24 |
| | Coupling agent | material | epoxy-based silane coupling agent | epoxy-based silane coupling agent | epoxy-based silane coupling agent | epoxy-based silane coupling agent |
| | | content (g) | 1.2 | 1.2 | 1.2 | 1.2 |
| | Surface-reflection inhibitor | material | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz | (1)nano-silica (hydrophilic) (2)nano-silica (hydrophobic) (3)sericite (4)quartz |
| | | content (g) | (1)1.6 (2)0.7 (3)0.8 (4)1.1 | (1)1.6 (2)0.7 (3)0.8 (4)1.2 | (1)1.6 (2)0.7 (3)0.8 (4)1.3 | (1)1.6 (2)0.7 (3)0.8 (4)1.4 |
| | | total content (g) | 4.1 | 4.1 | 4.1 | 4.1 |
| | Hardener | material | amine base | amine base | amine base | amine base |
| | | content (g) | 4 | 4 | 4 | 4 |
| Light-shielding film for optical element | Content (%) of inorganic black particle with a d-line refractive index of 2.2 to 3.5 | | 8 | 47 | 10 | 27 |
| | Thickness (μm) | | 5 | 5 | 5 | 5 |

In Comparative Example 1, light-shielding coating and film for optical element P, in which the dye content was decreased compared with that in Example 1, was used. As a result, in the light-shielding film for optical element of Comparative Example 1, the extinction coefficient was low, i.e., 0.02, and the inner-surface reflectance at incident angles of 45° and 36.73° was inferior. However, the deterioration of the inner-surface reflection at an incident angle of 68.13°, which is larger than the total reflection angle, was small. Flare and ghost were visually observed in evaluation of an image shot by the camera in which a lens provided with light-shielding film P was incorporated.

In Comparative Example 2, light-shielding coating and film for optical element Q, in which the dye content and the carbon content were increased compared with those in Example 3, was used. As a result, in the light-shielding film for optical element of Comparative Example 2, the extinction coefficient was high, i.e., 0.17, and the inner-surface reflectance at incident angles of 45° and 36.73° was inferior. Regarding the appearance, though roughness was observed, color tone was satisfactory. Flare and ghost were visually observed in evaluation of an image shot by the camera in which a lens provided with light-shielding film Q was incorporated.

Each physical property of light-shielding coating and light-shielding film Z, in which 8 wt % of carbon black-coated zirconia having a particle diameter of 20 nm was contained in the colorant unlike Example 17, is shown as Comparative Example 3 in Table 16. As a result, in the light-shielding film for optical element of Comparative Example 3, the extinction coefficient was low, i.e., 0.02, and the inner-surface reflectance at incident angles of 45° and 36.73° was inferior. Regarding the appearance, though roughness was observed, color tone was satisfactory. Flare and ghost were visually observed in evaluation of an image shot by the camera in which a lens provided with light-shielding film Z was incorporated.

Each physical property of light-shielding coating and light-shielding film AA, in which 47 wt % of carbon black-coated zirconia having a particle diameter of 20 nm was contained in the colorant unlike Example 17, is shown as Comparative Example 4 in Table 16. As a result, in the light-shielding film for optical element of Comparative Example 4, the extinction coefficient was high, i.e., 0.17, and the inner-surface reflectance at incident angles of 45° and 36.73° was inferior. Regarding the appearance, though roughness was observed, color tone was satisfactory. Flare and ghost were visually observed in evaluation of an image shot by the camera in which a lens provided with light-shielding film AA was incorporated.

Each physical property of light-shielding coating and light-shielding film AB, in which 10 wt % of TiN having a particle diameter of 20 nm was contained in the colorant unlike Example 20, is shown as Comparative Example 5 in Table 16. As a result, in the light-shielding film for optical element of Comparative Example 5, the extinction coefficient was low, i.e., 0.02, and the inner-surface reflectance at incident angles of 45° and 36.73° was inferior. Regarding the appearance, though roughness was observed, color tone was satisfactory. Flare and ghost were visually observed in evaluation of an image shot by the camera in which a lens provided with light-shielding film AB was incorporated.

Each physical property of light-shielding coating and light-shielding film AC, in which 27 wt % of TiN having a particle diameter of 20 nm was contained in the colorant unlike Example 16, is shown as Comparative Example 6 in Table 16. As a result, in the light-shielding film for optical element of Comparative Example 6, the extinction coefficient was high, i.e., 0.17, and the inner-surface reflectance at incident angles of 45° and 36.73° was inferior. Regarding the appearance, though roughness was observed, color tone was satisfactory. Flare and ghost were visually observed in evaluation of an image shot by the camera in which a lens provided with light-shielding film AC was incorporated.

TABLE 17

| | | | Comparative Example 1 | Comparative Example 2 |
|---|---|---|---|---|
| Evaluation of optical properties | Extinction coefficient | | 0.02 | 0.17 |
| | inner-surface reflectance (Ave. 400-700 nm %) | incident angle after refraction: 68.13° | 0.46 | 0.69 |
| | | incident angle after refraction: 45° | 0.07 | 0.08 |
| | | incident angle after refraction: 36.73° | 0.05 | 0.06 |
| | Degree of blackness | | 0.8 | 0.9 |
| | Appearance | | excellent | good |
| | Performance at fitting in lens barrel | | poor | poor |

TABLE 18

| | | | Comparative Example 3 | Comparative Example 4 | Comparative Example 5 | Comparative Example 6 |
|---|---|---|---|---|---|---|
| Evaluation of optical properties | Extinction coefficient | | 0.02 | 0.17 | 0.02 | 0.17 |
| | inner-surface reflectance (Ave. 400-700 nm %) | incident angle after refraction: 68.13° | 0.98 | 0.85 | 0.17 | 0.1 |
| | | incident angle after refraction: 45° | 0.08 | 0.08 | 0.08 | 0.08 |
| | | incident angle after refraction: 36.73° | 0.07 | 0.07 | 0.07 | 0.07 |
| | Degree of blackness | | 1 | 1 | 1 | 1 |
| | Appearance | | good | good | good | good |
| | Performance at fitting in lens barrel | | poor | poor | poor | poor |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-029514 filed Feb. 12, 2010 and No. 2011-002163 filed Jan. 7, 2011, which are hereby incorporated by reference herein in their entirety.

What is claimed is:

1. An optical element comprising a lens or a prism having a light-shielding film on an outer portion,
    wherein the light-shielding film comprises a resin and (i) a colorant and non-black particles having a refractive index (nd) of 2.2 or more or (ii) inorganic black particles having a refractive index (nd) of 2.2 or more and 3.5 or less,
    wherein the light-shielding film has an average thickness of 2 μm or more and 30 μm or less, and wherein the average of extinction coefficient of the light-shielding film for light having wavelengths ranging from 400 to 700 nm is 0.03 or more and 0.15 or less.

2. The optical element according to claim 1, wherein the colorant contains 20 wt% or more and 50 wt% or less of dye.

3. The optical element according to claim 1,
wherein the colorant contains dye and pigment; and
the pigment is composed of at least one selected from the group consisting of carbon black, copper-manganese complex oxide, titanium black, and copper oxide, each having an average particle diameter of 0.1 μm or more and 10 μm or less.

4. The optical element according to claim 1, wherein the light-shielding film contains non-black particles having an average particle diameter of 100 nm or less and a refractive index (nd) of 2.2 or more.

5. The optical element according to claim 1,
wherein the non-black particles contain titania, zirconia, or a mixture thereof.

6. The optical element according to claim 1,
wherein the inorganic black particles contain TiN, titania covered with carbon black, titania covered with titanium black, zirconia covered with carbon black, or zirconia covered with titanium black, having an average particle diameter of 100 nm or less.

7. The optical element according to claim 1,
wherein the ratio of a minimum transmittance to a maximum transmittance, (minimum transmittance)/(maximum transmittance), of the light-shielding film for light having wavelengths ranging from 400 to 700 nm is 0.7 or more.

8. The optical element according to claim 1,
wherein the light-shielding film has a difference in extinction coefficient thereof and is applied to an optical element in such a manner that the side having a smaller extinction coefficient than the average extinction coefficient of the light-shielding film is brought into the contact with the optical element.

9. The optical element according to claim 1,
wherein an inner-surface reflectance of inner-surface-reflected light, which is incident light having entered from the side of the optical element and having been reflected at an interface between the optical element and the light-shielding film and at an interface between the light-shielding film and air, at an incident angle of 36.73° is 0.05% or less, the inner-surface reflectance at an incident angle of 45° is 0.07% or less, and the inner-surface reflectance at an incident angle of 68.13° is 1% or less.

* * * * *